United States Patent [19]

Gold

[11] Patent Number: 5,015,856
[45] Date of Patent: May 14, 1991

[54] AUTOMATED PROCESS FOR PERMEABILITY DETERMINATIONS OF BARRIER RESINS

[75] Inventor: Harvey S. Gold, Newark, Del.

[73] Assignee: E. I. du Pont de Nemours and Company, Wilmington, Del.

[21] Appl. No.: 500,571

[22] Filed: Mar. 28, 1990

[51] Int. Cl.$^5$ .............................................. G01N 21/35
[52] U.S. Cl. .................... 250/339; 250/341; 356/51
[58] Field of Search ...................... 250/338.1, 339, 341, 250/358.1; 356/51

[56] References Cited

U.S. PATENT DOCUMENTS

| 4,423,327 | 12/1983 | Alexander | 250/358.1 |
| 4,791,296 | 12/1988 | Carpio | 250/339 |
| 4,800,279 | 1/1989 | Hieftje et al. | 250/339 |

FOREIGN PATENT DOCUMENTS

| 0285251 | 10/1988 | European Pat. Off. | 250/339 |
| 2556012 | 6/1977 | Fed. Rep. of Germany | 250/358.1 |
| 2311358 | 1/1977 | France | 250/358.1 |
| 64-88340 | 4/1989 | Japan | 250/339 |
| 8302158 | 6/1983 | World Int. Prop. O. | 356/51 |

OTHER PUBLICATIONS

Improved Selectivity in Spectroscopy by Multivariate Calibration, Martens et al., Journal of Chemometrics, vol. 1, 201–219 (1987).

Primary Examiner—Constantine Hannaher
Assistant Examiner—Jacob M. Eisenberg
Attorney, Agent, or Firm—Paul R. Steyermark

[57] ABSTRACT

Permeability of structures consisting essentially of dispersions of barrier resins in permeable structural resins can be predicted by the application of near infrared spectroscopy, within the wavelength range of 600–2500 nm, especially 1100–2500 nm. The method requires establishing a correlation between base permeabilities of samples of a Training set and their near infrared spectra, developing from that correlation a predictive equation, verifying the accuracy of the predictive equation on samples of a Validation set, and applying the predictive equation to the determination of the permeabilities of unknown samples.

18 Claims, 11 Drawing Sheets

FIG. I

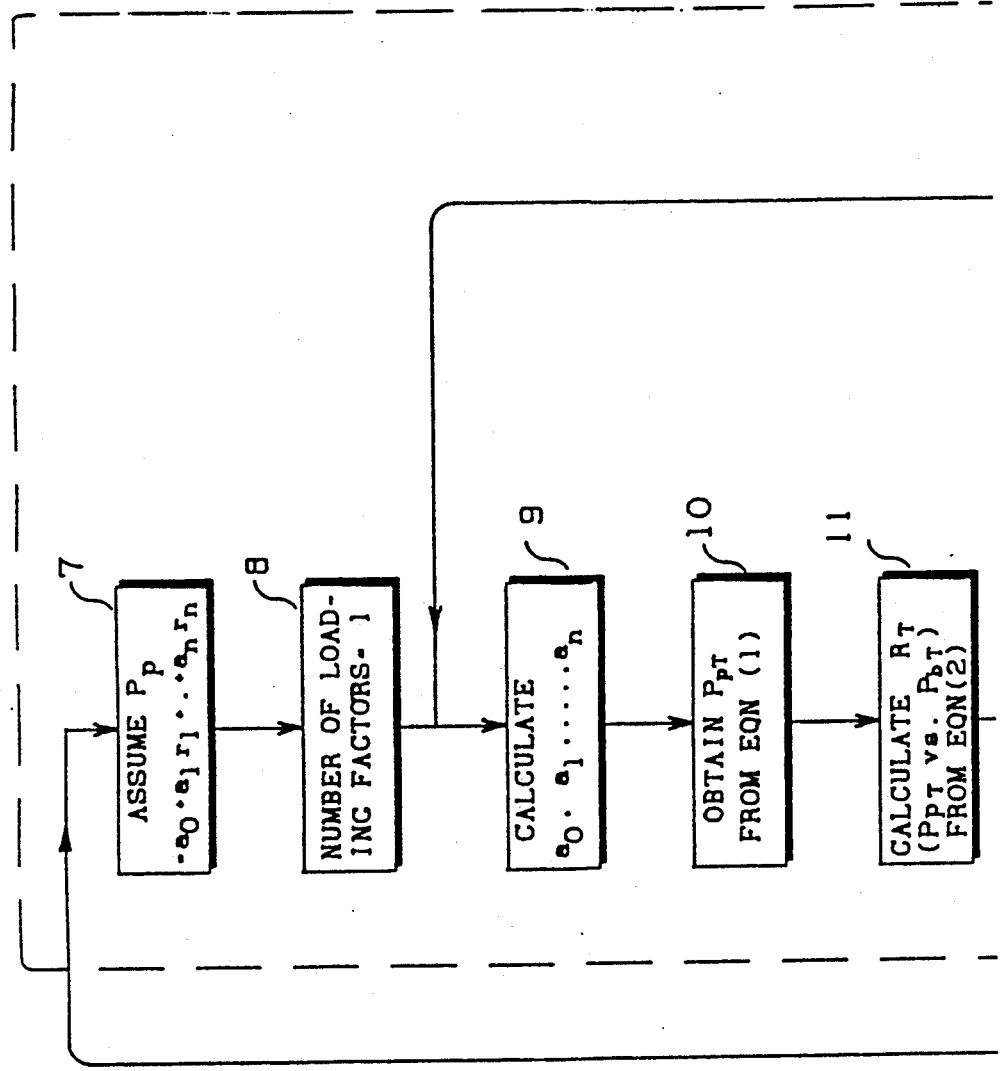
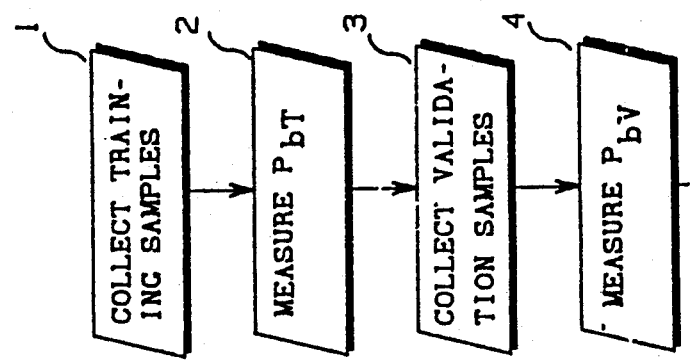
FIG. 5A

FIG. 7A
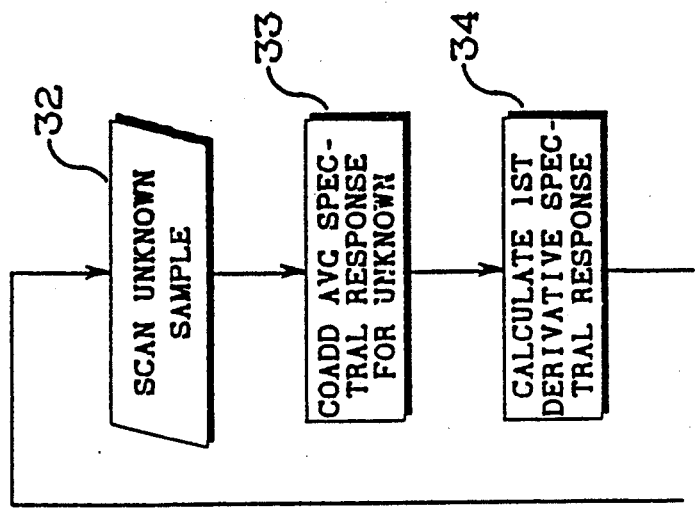
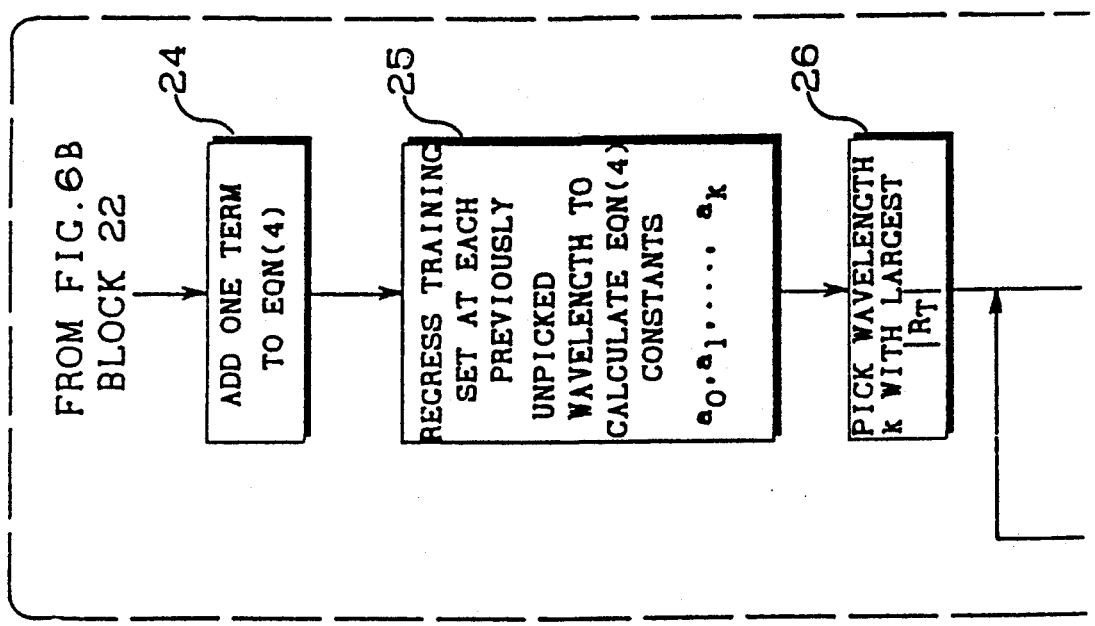

AUTOMATED PROCESS FOR PERMEABILITY DETERMINATIONS OF BARRIER RESINS

BACKGROUND OF THE INVENTION

This invention relates to a process for quickly and reproducibly determining the permeability of structures made of certain barrier resin compositions.

It is well known that certain resins such as, for example, polyamides, polyesters, polyvinyl alcohol, and ethylene/vinyl alcohol copolymers have low permeability to a variety of organic fluids, such as, for example, hydrocarbons and alcohols. Such resins, when used in applications where high permeability is undesirable, are often referred to as "barrier resins". In practical use, barrier resins are combined with resins having higher permeability to organic fluids but greater strength, especially greater impact strength, which in such applications are normally referred to as structural resins. Structures containing both a barrier resin and a structural resin are available in different forms. One such form is a laminar dispersion of barrier resin in a matrix of structural resin. Another is a composite containing at least one structural resin layer and at least one barrier resin layer, and which may in addition contain adhesive resin layers or layers of other materials. Barrier resin structures are very effective low permeability materials suitable for many uses, especially for containers such as bottles, paint cans, and gasoline tanks for automobiles. This last named use is growing very fast because substitution of plastic materials for metals effects weight savings, while at the same time eliminating gasoline tank corrosion. Additional advantages of gasoline tanks made of plastic materials are better utilization of available space, since such tanks can be molded in the exact desired shape, as well as the obvious superiority of blow molding plastic resins over bending and welding metal sheets. Many countries, including the United States, have approved in principle the use of synthetic materials in manufacturing gasoline tanks.

A container which is to be used for storage or transportation of liquids evolving potentially hazardous or environmentally undesirable vapors must be manufactured from a very low permeability material; and, in fact, certain permeability criteria have been developed and are embodied in various government and industrial standards. Permeability is affected by even subtle changes in process variables, so that, contrary to the intuitive expectations, it is impossible to accurately predict in advance the permeability of a given barrier resin structure from the barrier resin content in such a structure and the nominal process conditions. It is, therefore, necessary to be able to ascertain on a regular basis whether container production runs produce products which satisfy such standards. This normally is done by placing a given liquid in a container, closing the container, leaving it for a specified period at a specified temperature, and weighing the container with the liquid at reasonable intervals until the end of the specified period. This method of determining the container's permeability is rather tedious and slow; it is not well suited for making quick production run determinations.

It is, therefore, desirable to have available an automated, instrumental process for quickly and reliably determining container permeability, so that any departures from the standards can be readily recognized, and any necessary corrective action can be taken promptly.

SUMMARY OF THE INVENTION

According to this invention, there is provided a process for the determination of the permeability to organic fluids of a barrier resin structure comprising at least one barrier resin and at least one structural resin, said process involving the following steps:

(a) establishing by independent means the permeability of each one of a statistically meaningful number of samples, divided into a Training set and a Validation set, of a particular barrier resin structure to a particular organic fluid, such permeability being designated base permeability;

(b) making multiple scans at different locations of each sample of the Training set with a near infrared spectrometer operatively connected to a computer programmed to perform statistical analysis of data, to obtain by coaddition the spectral response of each sample—its transmittance, reflectance, or absorbance—at each wavelength within the range of about 600–2500 nm;

(c) statistically generating for the totality of the samples of the Training set a data matrix correlating their spectral responses at each wavelength with their base permeabilities previously established according to paragraph (a), to formulate a mathematical expression in the form of a predictive equation for calculating sample permeability from the spectral responses;

(d) verifying the accuracy of the predictive equation obtained in step (c) by applying the equation to calculate the predicted permeabilities of the Training set;

(e) measuring under the same conditions the spectral responses of the Validation set and applying the predictive equation obtained from the Training set to predict the permeability of each sample of the Validation set;

(f) comparing the predicted permeability of each sample of the Validation set with its base permeability established according to paragraph (a);

(g) if the results indicate that the predictive equation derived in step (c) does not predict the permeabilities of the Validation set at least as well as it predicts the permeabilities of the Training set, modifying the predictive equation in a statistically acceptable manner until it predicts the permeabilities of the Validation set at least to that degree;

(h) if the predicted permeabilities of the samples of the Training set are not within a predetermined degree of error from their previously established base permeabilities, further modifying the predictive equation in a statistically acceptable manner until the resulting predictive equation predicts the permeability of the Training set within the predetermined degree of error; and (i) measuring under the same conditions the spectral response of a barrier resin structure of unknown permeability and applying the above predictive equation to its spectral response, to predict the permeability of said structure.

BRIEF DESCRIPTION OF THE DRAWINGS

FIGS. 5A and 5B are block diagrams of one embodiment of the process of this invention, including a computer program, which can be used for implementing it.

FIGS. 6A, 6B, 7A, and 7B are block diagrams of another embodiment of the process of this invention, including a different computer program which can be used for implementing it.

DETAILED DESCRIPTION OF THE INVENTION

Figure 1:
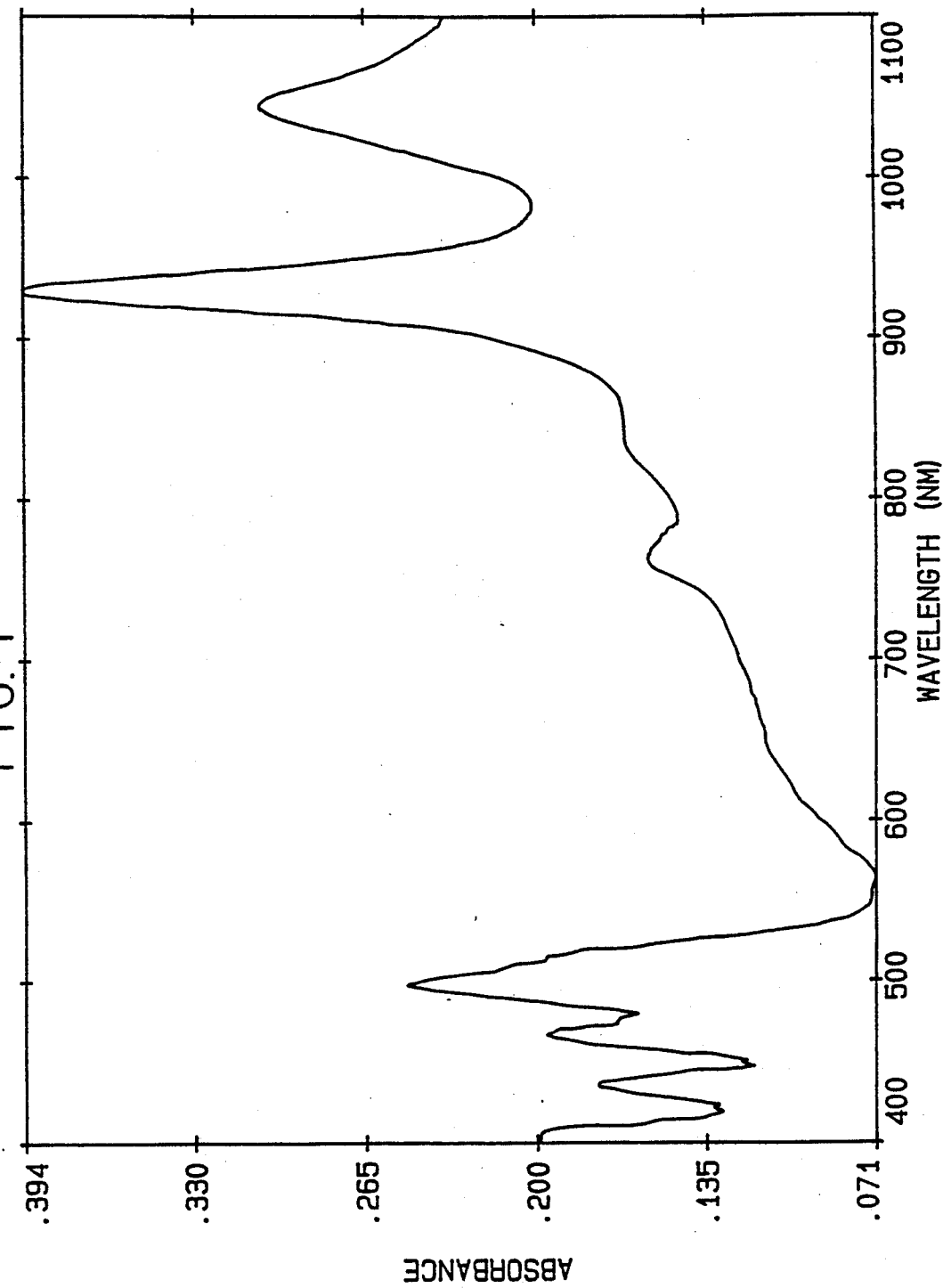
FIGS. 1 and 2 are typical near infrared spectroscopic scans of a so-called natural color barrier resin structure.

The term "structure" means a shaped article, which may be, for example, a container, a film, or a sheet. The term "container" is used in its broadest sense, to include any container that may be suitable for the storage or transport of fluids such as liquids or gases. In particular, this term will encompass, i.a., in addition to automobile gasoline tanks, such containers as bottles, cans, bags, pouches, tubes and pipes, tanks, and reservoirs. Films and sheets, of course, can be formed into containers. The structure of the highest importance is the container, but permeability determination need not be made on the whole container; it can be made on a fragment of a wall of the container, or of the film or sheet from which it was made. A whole container also can be subjected to its permeability determination according to this invention. In normal use, the container will be sealed or at least will be used in a manner which will minimize loss of fluid by simple evaporation, but this is neither a requirement nor a critical limitation of this invention.

The base permeability of a container can be most conveniently determined by weight loss under some standar time, temperature, and pressure conditions. The permeability of a film or sheet can be determined, e.g., by forming the film or sheet into a sealed container or by instrumentally analyzing the concentration of fluid in a chamber separated from the source of the fluid by a partition formed of the film or sheet.

Various barrier resin structures are known. Those include, i.a., laminar dispersions in structural resins and laminated or coextruded composite structures in which the barrier resin and the structural resin form separate layers, or a dispersion of barrier resin in structural resin which is laminated to a layer of the same or similar structural resin. Dispersions of barrier resins in permeable (structural) resins are known, for example, from U.S. Pat. Nos. 4,410,842 and 4,444,817 to P. M. Subramanian. Coextruded composite structures can be made, for example, as taught in U.S. Pat. Nos. 4,824,618 to Strum et al. and 4,800,129 to Deak.

This near infrared spectroscopy technique, although particularly suitable for the determination of permeability to fluids of barrier resins associated with structural resins, would not be normally applied to the determination of permeability of barrier resins alone or of structural resins alone. While the near infrared spectroscopic technique could be utilized for the measurement of the permeabilities of barrier resins alone, or of structural resins along, other, less expensive but reasonably fast techniques are available for that purpose.

Near infrared spectroscopy, however, is sensitive to the concentration and morphology of the barrier resin contained within the structural resin as well as to process conditions. It thus is commonplace to obtain different permeability values for compositionally identical barrier resin structures fabricated under slightly different conditions.

It is, therefore, a unique and outstanding characteristic of the process of this invention that it can quickly and accurately predict permeabilities of barrier resin structures under any process conditions and detect departures from the standards, thus making it possible to immediately adjust the process conditions to attain the desired permeability levels.

Typical barrier resins include, for example, polyesters such as poly(ethylene terephthalate) and poly(tetramethylene terephthalate), polyamides such as poly(hexamethylene adipamide), poly(epsilon-caprolactam), and copolymers of hexamethylene adipamide with epsilon-caprolactam, polyvinyl alcohol, copolymers of ethylene with vinyl alcohol, polyvinyl chloride, polyvinylidene chloride, and blends of two or more of the above resins; for example, blends of polyvinyl alcohol with a polyamide and of ethylene/vinyl alcohol copolymer with a polyamide.

Structural resins, as contemplated by this invention, are permeable to organic fluids, especially to hydrocarbon liquids and vapors. Typical structural resins are homopolymers and copolymers of alpha-olefins and of 1,3-dienes, and blends of two or more of the above resins as well as other hydrocarbon and chlorinated hydrocarbon resins having an alpha-olefinic unsaturation; for example, polyethylene, polypropylene, polyisobutylene, polychloroprene, polybutadiene, polystyrene, ethylene/propylene copolymers, and ethylene/propylene/1,3-butadiene terpolymers. All the typical structural resins and barrier resins are commercially available.

Near infrared (NIR) spectroscopy is conducted with specialized computerized equipment known as the near infrared (NIR) spectrometer. There are several suppliers of such equipment, including NIRSystems, Silver Spring, Md; L. T. Industries, Inc., Rockville, Md.; and Bran+Luebbe Analyzing Technologies, Elmsford, N.Y. The equipment vendors normally supply with their equipment operating software, which permits the user to operate his or her NIR spectrometer and to analyze the data. However, for the purpose of this invention, the computer program needs to be adapted or amplified to satisfy the requirements of this process, and this can be done in several ways.

The NIR spectrometer normally will be operated in either its transmittance or its reflectance mode. The former occurs when the source of near infrared radiation and the near infrared detector are located on the opposite sides of the sample, while the latter occurs when both the source and the detector are located on the same side of the sample. The transmittance mode may not be practical for thick or opaque samples or samples of filled or pigmented material. For these purposes, the so-called transflectance mode of operation, wherein a separate or integral reflector is employed, is considered to be a variant of the reflectance mode. Therefore, the reflectance mode will have potentially broader applications. The resulting response at each wavelength can be expressed in transmittance (T), reflectance, or absorbance (A) units, A being equal to log (1/T). When T=1, no absorption occurs; while, when T=0, infinite absorption occurs.

Figure 2:
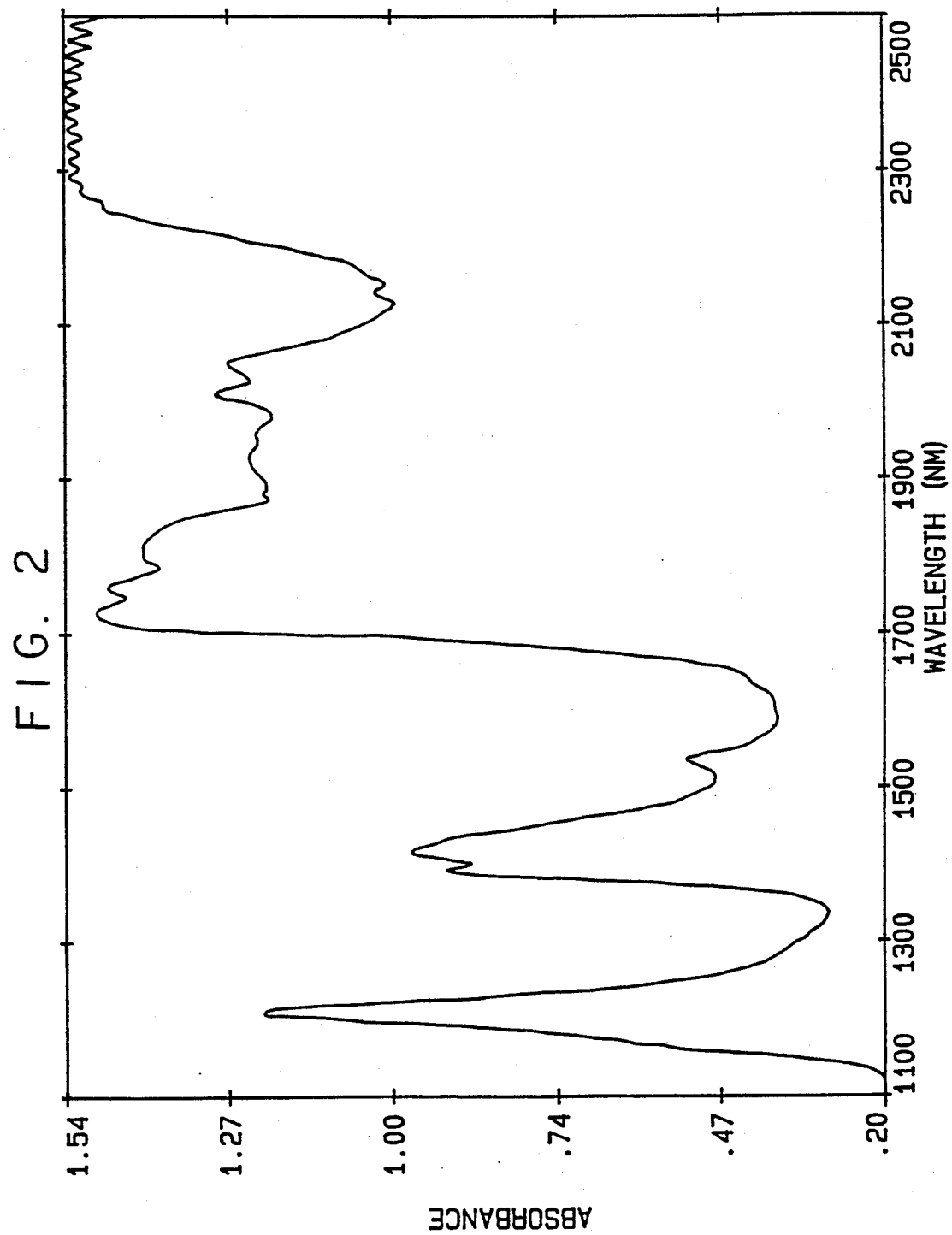
Figure 3:
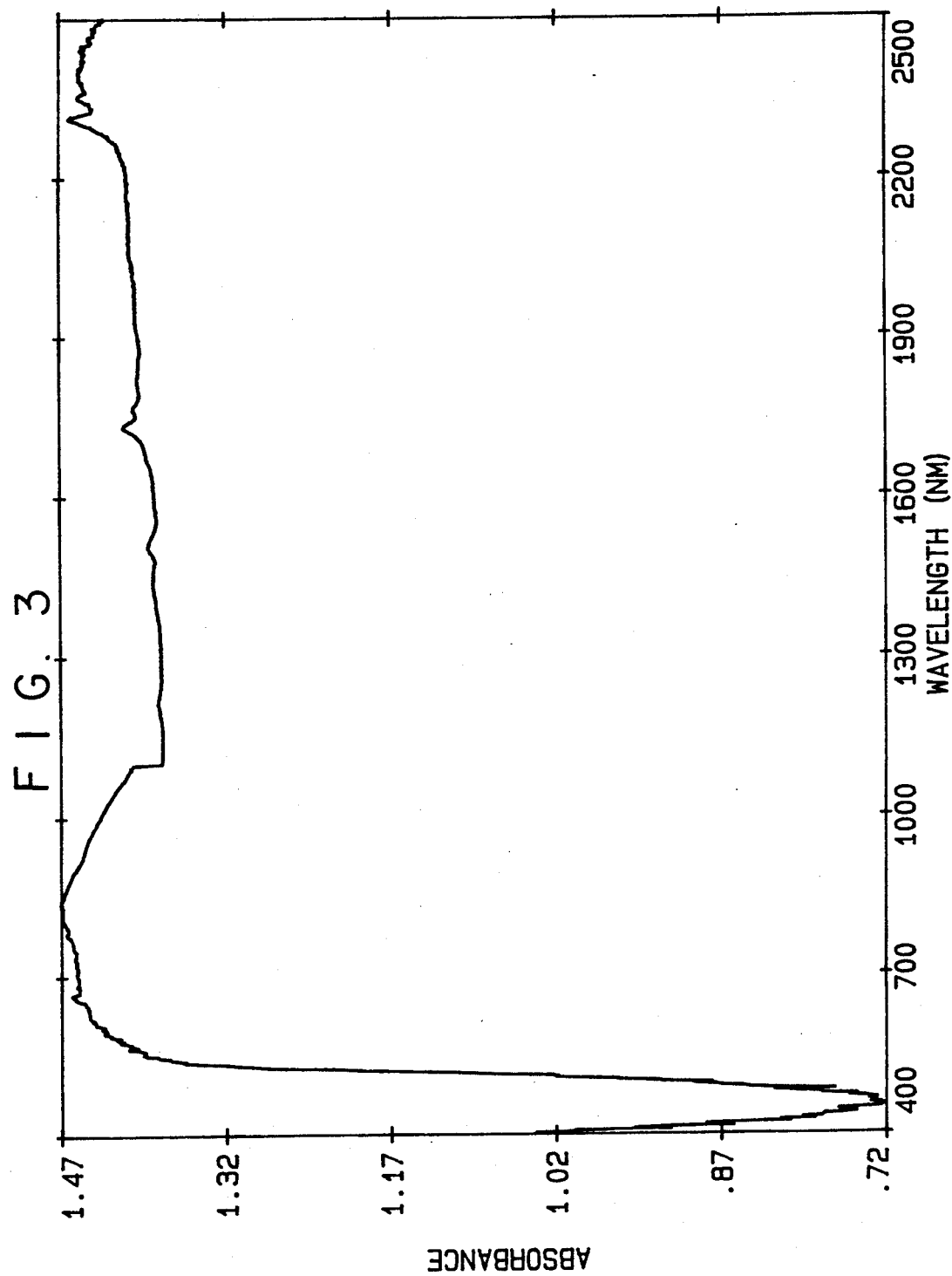
FIGS. 3 and 4 are typical near infrared spectroscopic scans of a so-called black barrier resin structure.

FIGS. 1 and 2 are typical NIR plots (usually referred to as NIR scans) of absorbance vs. wavelength. These particular scans were obtained for a structure made of a barrier resin composition consisting of a laminar dispersion prepared from a pelletized blend of 45.7 weight percent of polyamide and 54.3 weight percent of compatibilizer in polyethylene structural resin. The polyamide was made by condensing hexamethylenediamine, adipic acid, and epsilon-caprolactam in such weight ratios that the product contained 80% of poly(hexamethylene adipamide) and 20% of polycaproamide. The compatibilizer was high density polyethylene grafted with about 0.9 weight percent of fumaric acid. The dispersion contained 4 weight percent of the above barrier resin blend in 96 weight percent of high density polyethylene. The test structures were gasoline tanks, which were made by dry blending particles of the barrier resin blend and the structural resin and blow-molding at a melt temperature of 225°–230° C. The test fluid was xylene, and the permeability of the container to this fluid, determined by weight loss, was 33.4 grams per mm of sample thickness per day per 1 square meter of sample surface at 50° C. These gasoline tanks contained no pigment.

FIG. 1 represents the complete NIR scan over the wavelength range of less than 600 to 2500 nm, while FIG. 2 represents the preferred portion of the NIR scan from 1100 to 2500 nm. Absorbance is expressed in FIGS. 1–4 in Absorbance Units. One Absorbance Unit corresponds to a tenfold change in the transmittance of the sample relative to the reference signal. Transmittance is defined as the ratio of the radiant power transmitted by the sample to the radiant power incident on the sample. It is noted that absorbance exhibits over the indicated ranges several peaks and shoulders. The barrier resin structure in these scans was not pigmented and, therefore, is referred to as a natural color barrier resin structure.

Figure 4:
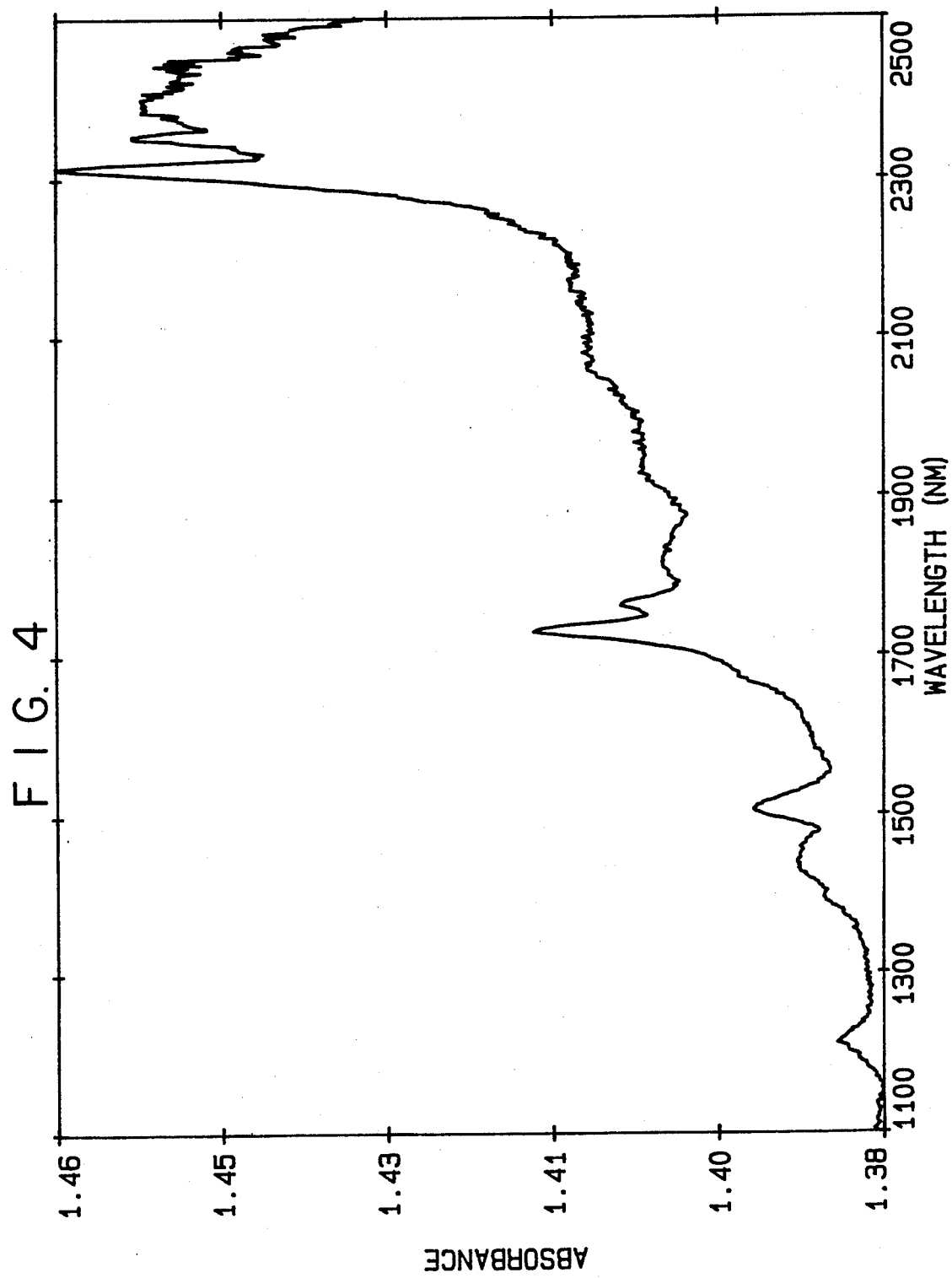

FIG. 3 again represents the complete NIR scan over the wavelength range of less than 600 to 2500 nm, while FIG. 4 represents the preferred portion of the NIR scan from 1100 to 2500 nm for a so-called "black" barrier resin structure, which was pigmented with carbon black. In this case, the scan of FIG. 3 appears to have considerably fewer peaks and valleys than the scan of FIG. 1, but this is due only to the scale of the plot, which also includes the very sharp minimum below 600 nm. When the 1100–2500 nm range is scaled up, as shown in FIG. 4, again numerous peaks and shoulders are observed. The particular barrier resin structure used in this experiment was the same as that used for the natural color samples shown in FIGS. 1 and 2.

The equipment used to generate the scan shown in FIG. 1 was NIR spectrometer Model 6500, supplied by NIRSystems, operatively connected to an IBM desktop computer PS/2 Model 50 loaded with software known as NSAS, also supplied by NIRSystems.

There are many well known mathematical techniques for correlation of NIR spectral responses to accomplish development of quantitative chemical analyses. They include, for example, "Single-Term Linear Regression", "Multiterm Linear Regression", "Component Spectrum Reconstruction", and "Discriminant Analysis" methods explained in an article by W. R. Hruschka at pp. 35–55 of *Near-Infrared Technology In The Agricultural And Food Industries*, P. C. Williams et al., Editors, American Association of Cereal Chemists, Inc., St. Paul, Minn., 1987 ("Williams"). Other techniques include, for example, "Hruschka Regression", "Fourier Transform Regression", "Principal Component Regression", and "Partial Least Squares Regression" methods explained in detail in an article by H. Martens et al. at pp. 57–87 of Williams. In Chapter 3 of *Multivariate Calibration*, H. Martens et al., John Wiley & Sons, Ltd., Chichester, U.K., 1989, more techniques, including for example, "Univariate Calibration", "Bilinear Modelling", "Self Deconvolution", "Target Transformation Factor Analysis", "Rank Annihilation Method", "Stepwise Multiple Linear Regression", "Ridge Regression", "Nonlinear Regression", and "Nonparametric Regression" are taught. The "Neural Network" technique explained in D. E. Rumelhart et al. in *Parallel Distributed Processing—Explorations in the Microconstruction of Cognition*, Vol. 1. *Foundations* 1986; Vol. 2. *Psychological and Biological Models*, 1986; and Vol. 3. *A Handbook of Models, Programs and Exercises*, 1988, MIT Press, Cambridge, Mass., may also be applied.

Although it is possible for a mathematician, scientist, or engineer to generate predictive equations for calculating permeability from NIR spectral scans of sample containers by applying the above mathematical techniques, either manually or by employing a self-contained computer program, it usually is simpler to employ computer programs supplied by manufacturers of NIR spectroscopy equipment. These programs provide data storage and retrieval as well as various data regression and report capabilities directly suited to the development of predictive equations from NIR spectral responses. Some commercially available software packages include, for example, "Near-Infrared Spectral Analysis Software" (NSAS) by NIRSystems, Inc., Silver Spring, Md.; "Unscrambler" by Camo A/S, Trondheim, Norway; "SpectraMetrix", "LightCal", and "LightCal Plus" by L. T. Industries, Inc., Rockville, Md.; "Spectra Calc" by Galactic Industries Corporation, Salem, N.H.; and "InfraAnalyzer Data Analysis System" (IDAS) and "Principal Component Analysis Program" (PCA-pc) by Bran+Luebbe Analyzing Technologies, Inc., Elmsford, N.Y.

Figure 5B:
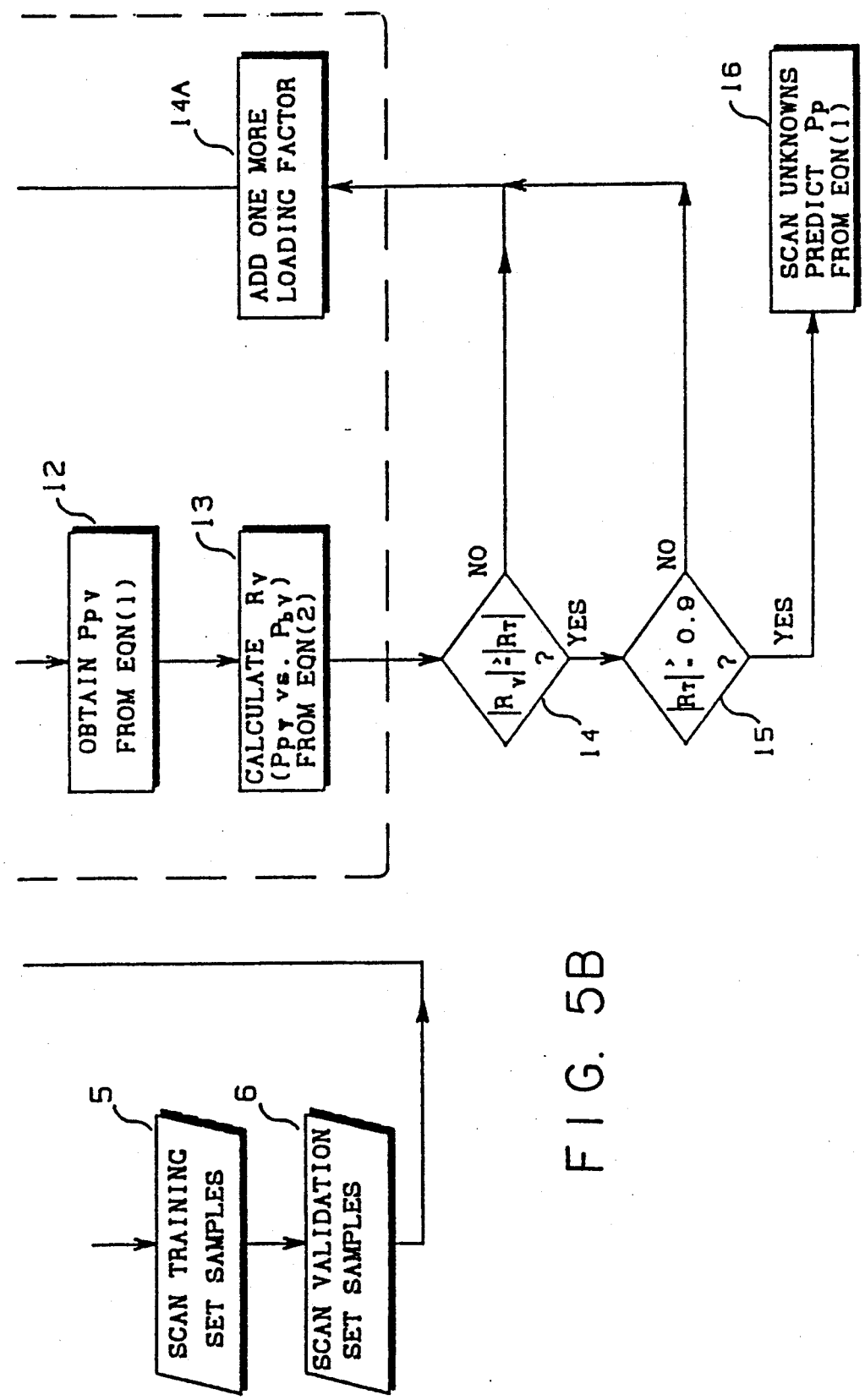

The preferred procedure for generating the permeability predictive equation uses the Partial Least Squares Regression (PLS) algorithms contained in NSAS version 3.07. FIGS. 5A and 5B represent a block diagram for this procedure, where the computer algorithm is enclosed within the broken lines.

Barrier resin structure samples expected to have permeabilities within a predetermined range (as estimated, for example, from known permeabilities of barrier resin structures having similar compositions) are divided into "Training" and "Validation" sets in such a way that each set contains a statistically valid number of samples the permeabilities of which span the entire range.

Base permeabilities, respectively, $P_{bT}$ and $P_{bV}$, of a representative number of Training set and Validation set samples are determined by conventional means, as shown in Blocks 1–4 in FIG. 5A. Obviously, it is immaterial to the success of this invention whether the samples are divided into the Training set and the Validation set before or after their base permeabilities have been determined.

All samples in these sets are scanned by NIR spectrometry within the selected range, either the full 600–2500 nm range or a smaller portion of the spectrum, usually 1100–2500 nm, as shown in Blocks 5 and 6 of FIG. 5B.

In the preferred practice of this invention, each scan over the NIR wavelength range is replicated, usually 32 times, once per second, and the average spectral response at each wavelength is recorded. The particular number of replicates and the scan repetition rate are largely dependent on the particular spectrometer employed and are not a critical limitation of this preferred practice. It is recommended that both the Training and Validation sets be scanned at several locations in order to reduce the importance of morphology and gross reflectivity variations caused by the shape of the container.

A predictive equation of the following form is assumed:

$$P_p = a_0 + a_1 \cdot r_1 + a_2 \cdot r_2 + \ldots + a_n \cdot r_n \quad (1)$$

where $P_p$ = predicted permeability of test fluid through the sample material;

$r_1, r_2, \ldots r_n$ = spectral responses at wavelengths 1, 2, ... n;

$a_0, a_1, a_2 \ldots a_n$ = constant coefficients.

This equation is the starting point of the algorithm employed by the computer; Block 7, FIG. 5A.

The PLS algorithm begins by presuming the existence of one loading factor; Block 8, FIG. 5A. Loading factors are related to the physical phenomena which contribute to production of error between the predicted permeability and base permeability. The PLS algorithm calculates the constant coefficients of the predictive equation (1) accounting for only one error-producing loading factor; Block 9, FIG. 5A. The predicted permeabilities for the Training set, $P_{pT}$, are calculated from the predictive equation (1); Block 10, FIG. 5A.

These $P_{pT}$ permeabilities are then compared with the respective base permeabilities, $P_{bT}$, of the same samples. Ideally, the relationship between the predicted and base permeabilities, when the pairs are ordered numerically from smallest to largest, is linear. Therefore, predicted and base permeabilities can be correlated by any standard statistical method, including linear least squares regression, and the quality of the correlation can be determined by numerical evaluation of one or more appropriate statistical parameters, such as, for example, the correlation coefficient and sum of the squares of the residuals. Although different techniques can be used for this correlation, comparison of correlation coefficients has been found very satisfactory and is recommended.

The correlation coefficient, $R_T$, of the Training set is first evaluated, as shown in Block 11 of FIG. 5A. By the term "correlation coefficient" is meant the Pearson product moment correlation coefficient, R, which is a well known statistical value for measuring the association between two variables and which is calculated according to the following equation (2):

$$R = \frac{m \cdot \sum_{j=1}^{m}(X_j \cdot Y_j) - \sum_{j=1}^{m}(X_j) \cdot \sum_{j=1}^{m}(Y_j)}{\sqrt{m \cdot \sum_{j=1}^{m}(X_j^2) - \sum_{j=1}^{m}(X_j)^2} \cdot \sqrt{m \cdot \sum_{j=1}^{m}(Y_j^2) - \sum_{j=1}^{m}(Y_j)^2}} \quad (2)$$

where
R = correlation coefficient
m = number of samples
$X_j$ = j-th value of variable X
$Y_j$ = j-th value of variable Y As applied to this invention, X is the predicted permeability, $P_p$; Y is the base permeability, $P_b$; and m is the number of averaged scans.

Similarly, predicted permeabilities, $P_{pV}$, for the Validation set samples are obtained from Equation (1), as in Block 12, FIG. 5B. They are then statistically correlated with the respective base permeabilities of this set, the correlation coefficient for the validation set, $R_V$, being calculated from the above Equation (2). This is shown in Block 13 of FIG. 5B.

The statistical quality parameters for the correlation of base and predicted Training set permeabilities are compared to the similarly obtained parameters of the Validation set. In the particular case illustrated in FIGS. 5A and 5B, the correlation coefficients $R_T$ and $R_V$ are compared; see Block 14, FIG. 5B. If the Validation set correlation is not at least as good as the Training sample set correlation (that is, if the absolute value of $R_V$ is smaller than the absolute value of $R_T$), either the system operator or the computer program itself instructs the PLS algorithm to add a further loading factor and repeat the numerical procedure for calculating new predictive equation constant coefficients (Block 14A, FIG. 5B). This process is repeated until the correlation between the predicted and base permeabilities of the Validation set is at least as good as the correlation of the Training set, from which it was derived.

The correlation coefficient of the Training set, $R_T$, is next evaluated to determine whether the quality of the predictive equation is satisfactory for the intended application, Block 15 of FIG. 5B. It is a well understood principle of statistics that the absolute value of the correlation coefficient will increase and approach unity as the quality of the predictive equation improves. It is the preferred practice to test whether the predictive equation produces a correlation coefficient at least equal to 0.9. If not, either the system operator or the computer program itself instructs the PLS algorithm to add a further loading factor and repeat the numerical procedure for calculating new predictive equation constant coefficients. When the correlation coefficient is at least 0.9, the calibration procedure is complete. Unknown samples can now be scanned, as shown in Block 16 of FIG. 5B, and the predictive equation can be used to calculate permeability.

Naturally, one may elect to accept predictive equations which produce lower correlation coefficients than 0.9 for less critical applications, but even in that case the same general procedure would be used.

The relative order in which the operations of Blocks 14 and 15 of FIG. 5B are performed is not critical; one may prefer to first determine whether $R_T$ is at least 0.9; if it is not, add further load factors until this result is obtained, and only then compare the absolute values of $R_T$ and $R_V$. Likewise, Block 15 may be placed between Blocks 11 and 12, if desired, instead of following Block 14 or 13.

Since Training set samples are preferably scanned at multiple locations, the PLS technique can minimize the prediction error attributed to scanning at different locations on samples by adding sufficient loading factors. Therefore, it is sufficient to scan unknown samples at only one location, thus making application of this invention to on-line production quality control simple, quick, and economical.

Another technique for defining a predictive equation for calculating permeability from NIR measurements uses the Stepwise Multiple Regression (SMR) method implemented by the "Standard Regression" algorithm of the NSAS computer software. A block flow diagram for this procedure is shown in FIGS. 6A, 6B, 7A, and 7B, where the computer algorithm is enclosed by broken lines.

Figure 6A:
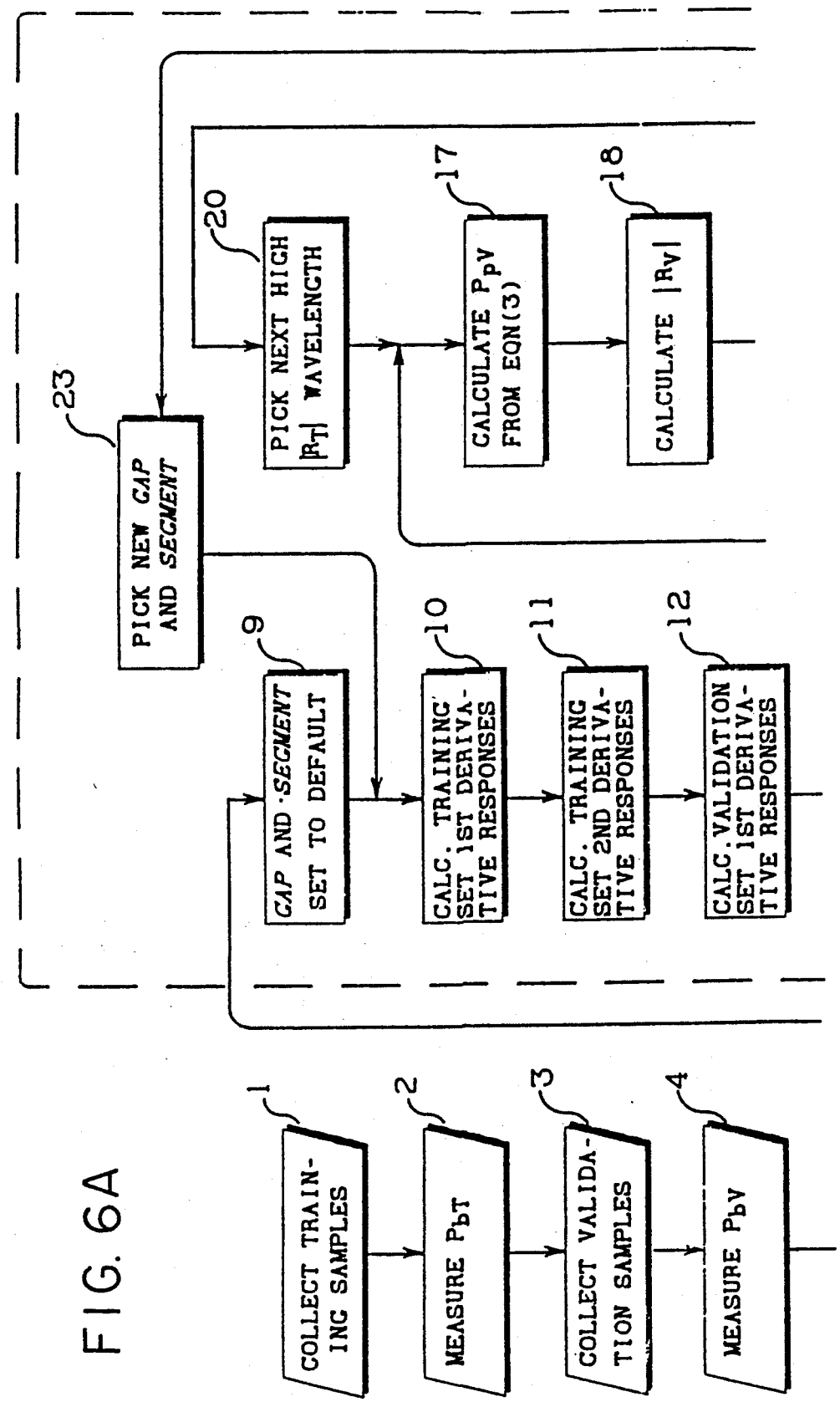

In the SMR technique, the initial steps of selecting Training and Validation set samples and establishing their base permeabilities, $P_b$, are the same as in the PLS technique and as shown in Blocks 1–4 of FIG. 6A. Each Training set sample is scanned by the NIR spectrometer (Block 5, FIG. 6B). Preferably each NIR wavelength range scan is repeated multiple times, most preferably 32 times, once per second, and the average spectral response at each wavelength is recorded. It is a further preferred practice to scan sample structures at multiple positions. The coadded average spectral response for each Training sample structure is calculated (Block 6, FIG. 6B) by computing the sum of the recorded spectral responses at each wavelength obtained from the scans at each structure position and dividing the sum by the number of positions scanned. For example, assume that a sample structure in the form of a cube-shaped container is scanned at six positions, (that is, its top, bottom, and four sides); then the six recorded spectral responses at 600 nm would be summed and divided by 6 to obtain the coadded average spectral response at 600 nm; the six recorded spectral responses at 601 nm would be summed and divided by 6 to obtain the coadded average spectral response at 601 nm, etc.

Figure 6B:
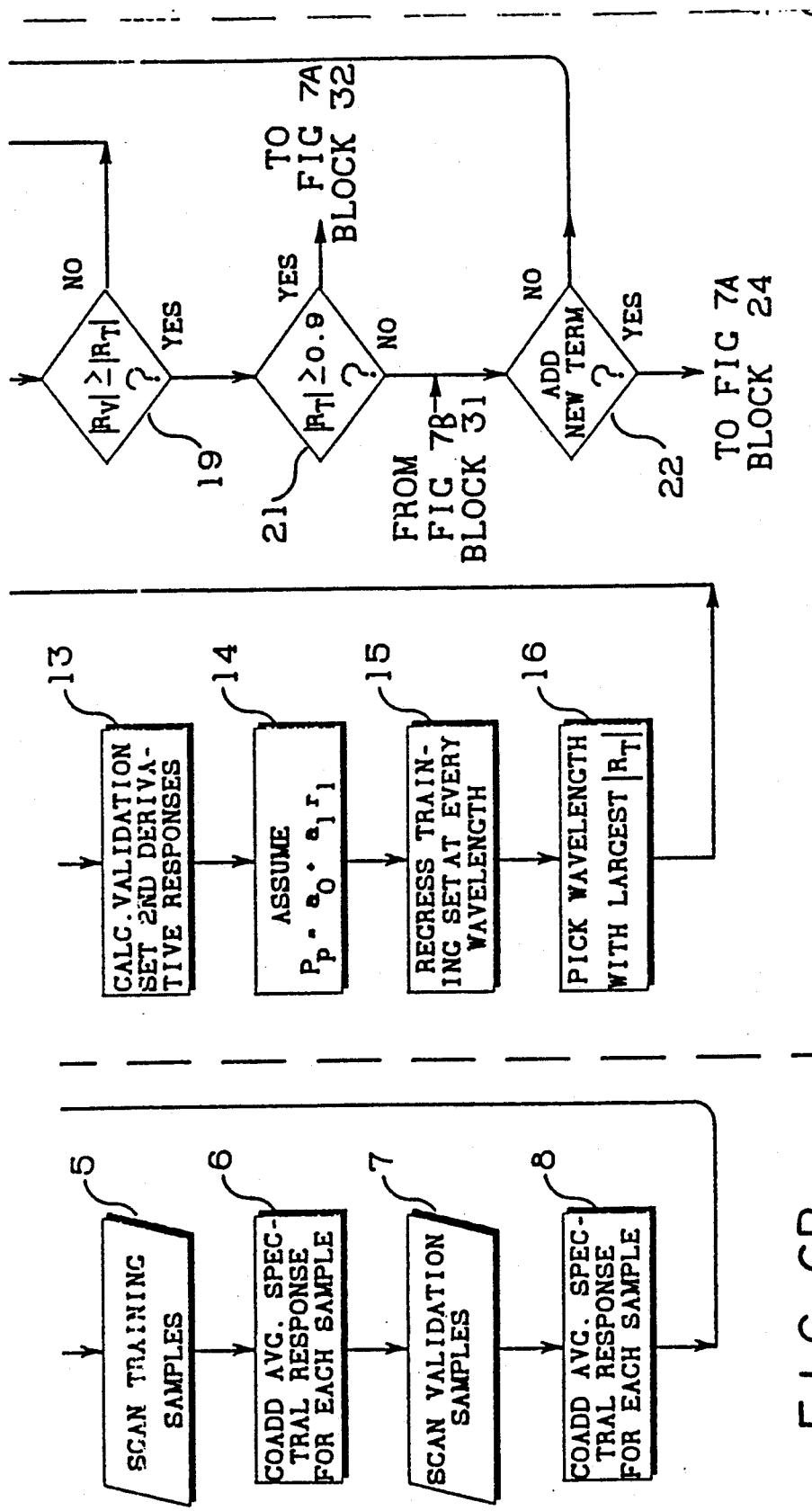

Validation set sample structures are each similarly scanned at multiple positions and multiple times at each position, and the coadded average for each sample structure is calculated, as shown in Blocks 7–8 of FIG. 6B.

The SMR method may be applied to the coadded average spectral responses directly. Practice has shown that the spectral responses when plotted against wavelength, as shown in FIGS. 1–4, for typical barrier resin structures, produce plots having shifting baselines (that is, the baseline from which the peaks rise, appears to shift across the wavelength range). It is a preferred practice of the SMR method to minimize or eliminate the error introduced by shifting baselines by correlating permeability to the first and second derivatives of coadded spectral response. Many derivative calculation techniques are available in numerical analysis literature to calculate derivatives of the plot of coadded spectral response versus wavelength. The method implemented by the NSAS version 3.07 "Standard Regression" algorithm requires selection of "gap" and "segment" parameters. The algorithm automatically selects an initial set of "gap" and "segment" parameters by default (Block 9 of FIG. 6A), from which the first and second derivatives of the plots of spectral response versus wavelength are calculated (Blocks 10–12, FIG. 6A; Block 13, FIG. 6B).

As shown in Block 14 of FIG. 6B, the SMR method initially postulates a predictive equation of the form:

$$P_p = a_0 + a_1 \cdot r_1 \quad (3)$$

where
$P_p$ = permeability of test fluid through barrier resin structure;
$r_1$ = second derivative of spectral response at wavelength 1;
$a_0$ and $a_1$ = constant coefficients.

Values for constant coefficients are calculated by standard regression analysis of the data matrix consisting of the base permeabilities and second derivative spectral responses at each wavelength for each Training set sample; see Block 15 of FIG. 6B. All the Training set base permeabilities, $P_{bT}$, thus are paired with the corresponding second derivative spectral responses at the first wavelength of the scanned range, and standard regression methods, such as linear least squares regression, are used to calculate the constant coefficients. Predicted permeability for each Training set sample, $P_{pT}$, can be calculated from equation (3). All the predicted permeabilities and corresponding base permeabilities of Training set samples can be processed according to equation (2) to obtain a correlation coefficient, $R_T$. This regression procedure is repeated for each wavelength of the scanned range, in turn. The wavelength which produces the largest absolute value of the correlation coefficient, $|R_T|$, is chosen as wavelength No. 1 of equation (3), as shown in Block 16 of FIG. 6B.

According to Blocks 17–18 of FIG. 6A and 19 of FIG. 6B, the Validation set samples are used to evaluate the quality of the predictive equation. Having identified wavelength No. 1 and constant coefficients, the predicted permeabilities of the Validation set samples, $P_{pV}$, can be evaluated from equation (3). Validation set predicted and base permeabilities are processed using equation (2) to obtain the correlation coefficient, $R_V$. If the Validation set correlation is not at least as good as the Training sample set correlation (that is, if the absolute value of $R_V$ is smaller than the absolute value of $R_T$), then the initial selection of wavelength No. 1 was not appropriate. The system operator must select from among the wavelengths considered in Block 16 the wavelength which provides the next largest absolute value of the Training set correlation coefficient, $|R_T|$, for the Training set, as shown in Block 20 of FIG. 6A. The procedure of Blocks 20 and 17–19 is repeated until a wavelength is found at which the correlation between the predicted and base permeabilities of the Validation set is at least as good as the correlation of the Training set, from which it was derived.

The correlation coefficient of the Training set, $R_T$, is next evaluated to determine whether the quality of the predictive equation is satisfactory for the intended application (Block 21 of FIG. 6B). As in the PLS method, it is the preferred practice to test whether the predictive equation produces a correlation coefficient having an absolute value of at least 0.9. If it does, the predictive equation is deemed sufficiently accurate to be applied to unknown samples. The system operator can proceed to steps, represented by Blocks 32–34 of FIG. 7A and 35–36 of FIG. 7B, in which unknown samples are scanned; the coadded spectral responses and second derivative responses are calculated; and permeabilities are determined from the predictive equation.

If the absolute value of the correlation coefficient for the predicted and base permeabilities of the Training set, $|R_T|$, is smaller than 0.9, as shown in Block 21 of FIG. 6B, a statistical technique is employed to determine whether addition of a term to the predictive equation (3) (that is, addition of a contribution from spectral response at another wavelength) is justified; see Block 22 of FIG. 6B. One such statistical test is based upon the weighted sums of squared residuals for each prospective model and is described in *Statistical Treatment of Experimental Data*, Chapter 15, pp. 332–341, by J. R. Green et al., Elsevier Scientific Publishing Company, New York, 1978. If addition of another term is not justified, new "gap" and "segment" parameters are selected by the system operator (Block 23, FIG. 6A), and the entire process of Blocks 10–21 is repeated. If statistical analysis justifies adding a term to the predictive equation, SMR postulates an equation with one additional term (Block 24 of FIG. 7A) of the form of equation (4):

$$P_p = a_0 + a_1 \cdot r_1 + a_2 \cdot r_2 + \ldots + a_k \cdot r_k \qquad (4)$$

where $P_p$=permeability of fluid through barrier resin structure;

$r_1, r_2, \ldots r_k$=derivative (usually, second derivative) spectral responses at wavelength number k;

$a_0, a_1, a_2, \ldots a_k$=constant coefficients;

k=k-th numbered term of the equation.

When a k-th term is added to the predictive equation, previous, lower numbered wavelength selections, (that is, wavelengths numbered $1, 2, \ldots, k-1$) are retained. Standard multivariable linear regression techniques are applied to the matrix data arrays of the Training set base permeabilities and corresponding second derivative spectral responses at k wavelengths to calculate new constant coefficients $a_0, \ldots, a_k$ for predictive equation (4). The matrix data arrays are:

$$\begin{bmatrix} P_{bT1} \\ P_{bT2} \\ P_{bT3} \\ \cdot \\ \cdot \\ \cdot \\ P_{bTm} \end{bmatrix} \quad \begin{bmatrix} r_{11} r_{12} r_{13} \cdots r_{1k} \\ r_{21} r_{22} r_{23} \cdots r_{2k} \\ r_{31} r_{32} r_{33} \cdots r_{3k} \\ \cdot \quad \cdot \quad \cdot \quad \cdot \\ \cdot \quad \cdot \quad \cdot \quad \cdot \\ \cdot \quad \cdot \quad \cdot \quad \cdot \\ r_{m1} r_{m2} r_{m3} \cdots r_{mk} \end{bmatrix}$$

where $P_{bTm}$=base permeability of the m-th Training set sample, and $r_{mk}$=second derivative spectral response of the m-th Training set sample at the k-th wavelength.

For example, assume that 1250 nm, 900 nm, 2200 nm, and 1500 nm had been selected as wavelengths 1–4 and it was required to add a term to predictive equation (4). The second derivative spectral response at 600 nm is tentatively substituted for $r_{mk}$. Linear regression is applied to the data matrices to identify constant coefficients $a_0$–$a_5$. The predicted permeabilities, $P_{pT}$, for each Training set sample are calculated from equation (4). All the predicted permeabilities and corresponding base permeabilities of the Training set samples can be processed according to equation (2) to obtain a correlation coefficient, $R_T$. This regression procedure (Block 25, FIG. 7A) is repeated substituting 601 nm and each wavelength of the scanned range except 1250 nm, 900 nm, 2200 nm, and 1500 nm, in turn, for wavelength k=5.

The wavelength which produces the largest absolute value of the correlation coefficient, $R_T$, is chosen as wavelength number k of equation (4), as shown in Block 26 of FIG. 7A.

Figure 7B:
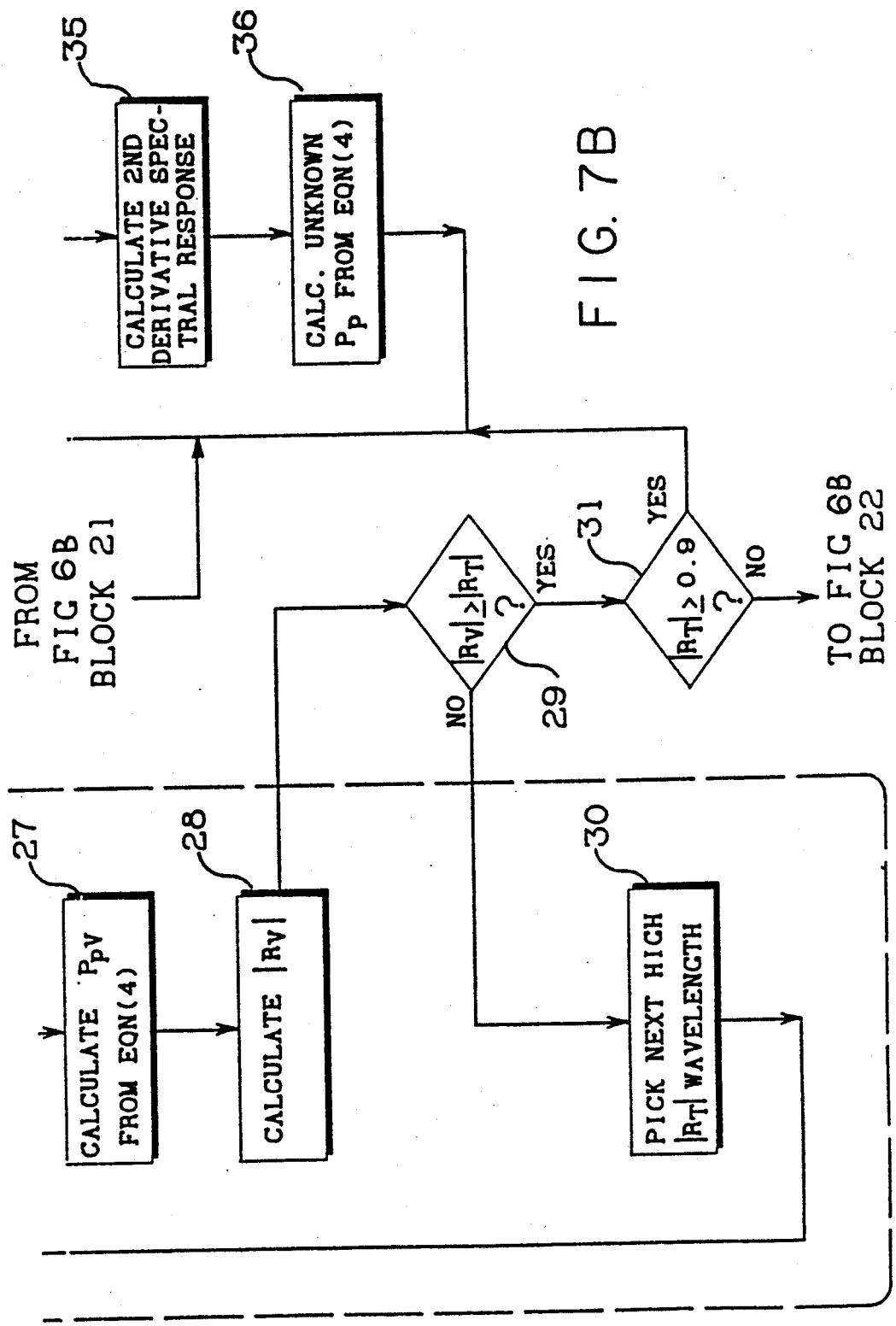

After the constant coefficients have been calculated for equation (4) that provides the highest $R_T$ for second derivative spectral responses at k specified wavelengths, the predicted permeabilities for the Validation set samples can be calculated (Block 27, FIG. 7B). Predicted and base permeabilities of the Validation set are processed using equation (2) to obtain the correlation coefficient, $R_V$ (Block 28, FIG. 7B). If the Validation set correlation is not at least as good as the Training set correlation (that is, if the absolute value of $R_V$ is smaller than the absolute value of $R_T$), then the initial selection of wavelength k was not appropriate (Block 29, FIG. 7B). Another, previously unselected wavelength, which provides the next highest correlation coefficient for Training set predicted and baseline permeabilities is selected as wavelength k (Block 30, FIG. 7B). The steps represented by Blocks 27–29 and 30 in FIG. 7B are repeated until predictive equation constant coefficients, $a_0 \ldots a_k$, are found which cause the equation to predict Validation set sample permeability at least as well as Training set sample permeability.

The correlation coefficient of the Training set, $R_T$, is next evaluated to determine whether the quality of the predictive equation is satisfactory for the intended application; Block 31, FIG. 7B. As before, it is the preferred practice to test whether the predictive equation produces a correlation coefficient having an absolute value of at least 0.9. If it does, the predictive equation is deemed sufficiently accurate to be applied to unknown samples. The system operator can proceed to the steps of Blocks 32–34 of FIG. 7A and 36—36 of FIG. 7B, in which unknown samples are scanned; the coadded spectral responses and second derivative responses are calculated; and permeabilities are determined from the predictive equation (4).

If, however, the absolute value of the Training set correlation coefficient is less than 0.9, the predictive equation (4) must be further redefined by returning to the step of Block 22 of FIG. 6B.

When using the SMR method, it is possible to scan unknown samples at single positions; however, it is preferred to employ the multiple-position scanning and coadded averaging procedures for unknown samples in the same way as done for the Training and Validation set samples.

Figure 8:
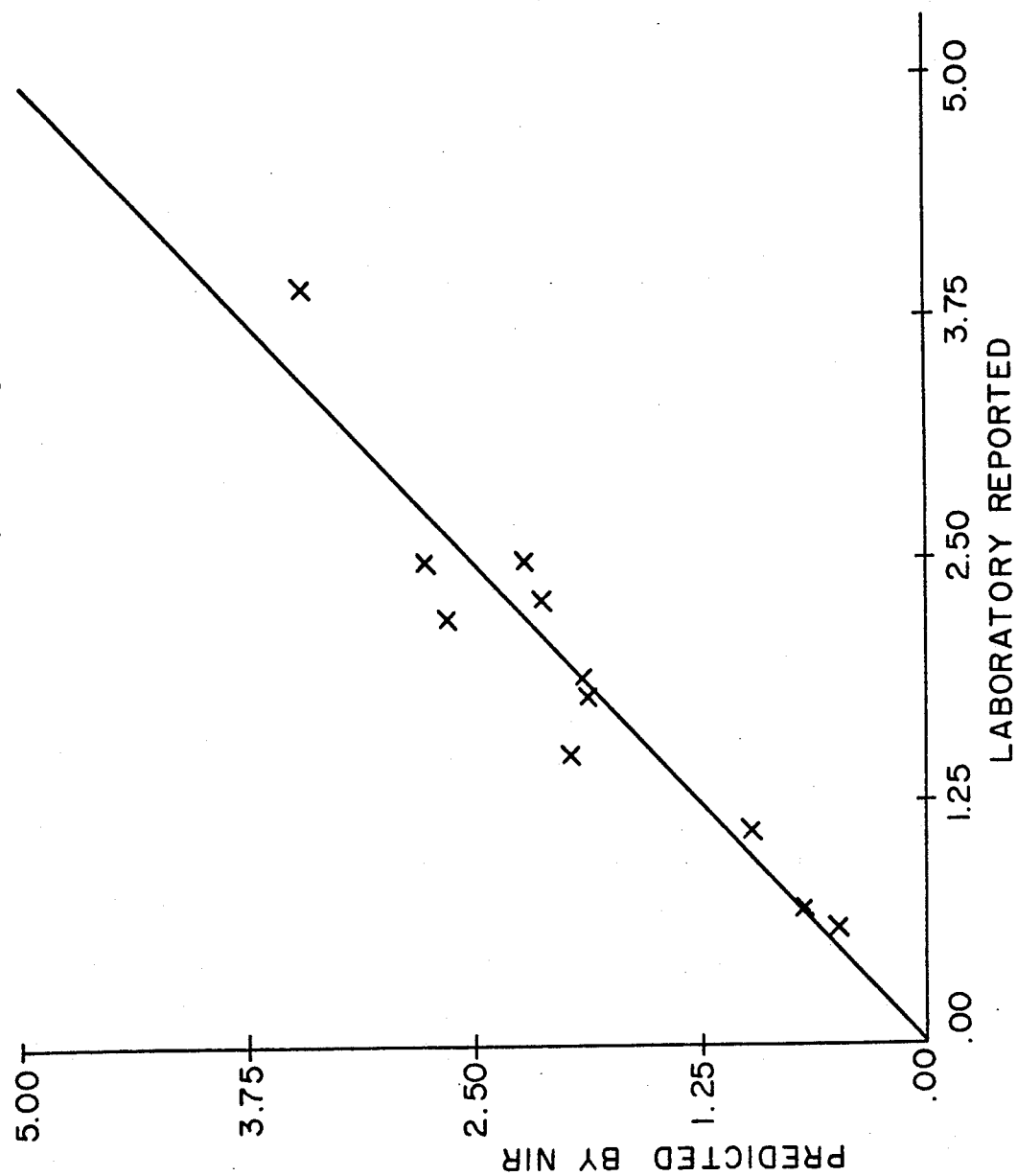
FIG. 8 is a plot of barrier resin structure permeabilities determined according to this invention vs. those determined by an independent laboratory technique for a number of different samples of laminar barrier resin dispersion in structural resin.

FIG. 8 is a plot of barrier resin structure permeability calculated for experimental gasoline tanks from NIR spectra according to the present invention vs. the independently established base permeability of samples of a natural color laminar dispersion of 7 weight percent of the same barrier resin blend in 93 weight percent of high density polyethylene as was used earlier for the purpose of FIGS. 1 and 2. The permeability data are expressed in grams of fluid per gasoline tank per day at 40° C. Each X in this plot corresponds to a run in which some process variable was changed.

Barrier properties depend not only on the amount of barrier resin in the dispersion but also on the degree to which the proper fabricating conditions have been attained. The extrusion/blow-molding conditions must result in a proper lamellar barrier structure. Variations in process temperature, shear conditions, extruder operating parameters, etc., lead to markedly different barrier properties. This is why a good quality control method is required. The data presented in FIG. 8 represent a run where extruder/blow-molding conditions were either deliberately or unintentionally varied, so that the samples would have varying permeabilities despite a constant barrier resin content in the dispersion. It can be seen that the plot, extrapolated by the least squares method, is a straight line, starting at the origin of the system of coordinates and bisecting the system of coordinates at a 45° angle. This confirms the applicability of the process of the present invention to the prediction of permeabilities of compositionally identical samples fabricated under different conditions.

I claim:

1. Process for the determination of the permeability to organic fluids of a barrier resin structure comprising at least one barrier resin and at least one structural resin, said process involving the following steps:

(a) establishing by independent means the permeability of each one of a statistically meaningful number of samples, divided into a Training set and a Validation set, of a particular barrier resin structure to a particular organic fluid, such permeability being designated base permeability;

(b) making multiple scans at different locations of each sample of the Training set with a near infrared spectrometer operatively connected to a computer programmed to perform statistical analysis of data, to obtain by coaddition the spectral response of each sample—which is its transmittance, reflectance, or absorbance—at each wavelength within the range of about 600–2500 nm;

(c) statistically generating for the totality of the samples of the Training set a data matrix correlating their spectral responses at each wavelength with their base permeabilities previously established according to paragraph (a) to formulate a mathematical expression in the form of a predictive equation for calculating sample permeability from the spectral responses;

(d) verifying the accuracy of the predictive equation obtained in step (c) by applying the equation to calculate the predicted permeabilities of the Training set;

(e) measuring under the same conditions the spectral responses of the Validation set and applying the predictive equation obtained from the Training set to predict the permeability of each sample of the Validation set;

(f) comparing the predicted permeability of each sample of the Validation set with its base permeability established according to paragraph (a);

(g) if the results indicate that the predictive equation derived in step (c) does not predict the permeabilities of the Validation set at least as well as it predicts the permeabilities of the Training set, modifying the predictive equation in a statistically acceptable manner until it predicts the permeabilities of the Validation set at least to that degree;

(h) if the predicted permeabilities of the samples of the Training set are not within a predetermined degree of error from their previously established base permeabilities, further modifying the predictive equation in a statistically acceptable manner until the resulting predictive equation predicts the permeability of the Training set within the predetermined degree of error; and (i) measuring under the same conditions the spectral response of a barrier resin structure of unknown permeability and applying the above predictive equation to its spectral response, to predict the permeability of said structure.

2. The process of claim 1, wherein at least some near infrared scans are made only within the wavelength range of about 1100–2500 nm.

3. The process of claim 1 wherein the spectral response of each sample is measured as the sample's reflectance.

4. The process of claim 1 wherein the sample structure is a laminar dispersion of barrier resin in a structural resin.

5. The process of claim 1 wherein the sample structure is a laminate comprising at least one layer of barrier resin and at least one layer of structural resin.

6. The process of claim 1 wherein the sample structure is a laminate comprising at least one layer of a laminar dispersion of barrier resin in structural resin and at least one layer of the same structural resin.

7. The process of claim 4 wherein the sample structure is pigmented.

8. The process of claim 7 wherein the sample structure is pigmented with carbon black.

9. The process of claim 4 wherein the barrier resin is at least one member selected from the group consisting of polyvinyl alcohol, ethylene/vinyl alcohol copolymers, polyester, polyamides, polyvinyl chloride, and polyvinylidene chloride.

10. The process of claim 9 wherein the structural resin is at least one member selected from the group consisting of homopolymers and copolymers of alpha-olefins and of 1,3-dienes, polystyrene, and polychloroprene.

11. The process of claim 10 wherein the structural resin is a homopolymer of an alpha-olefin or a copolymer of at least two alpha-olefins.

12. The process of claim 5 wherein the sample structure is pigmented.

13. The process of claim 12 wherein the sample structure is pigmented with carbon black.

14. The process of claim 6 wherein the sample structure is pigmented.

15. The process of claim 14 wherein the sample structure is pigmented with carbon black.

16. The process of claim 5 wherein the barrier resin is at least one member selected from the group consisting of polyvinyl alcohol, ethylene/vinyl alcohol copolymers, polyesters, polyamides, polyvinyl chloride, and polyvinylidene chloride.

17. The process of claim 16 wherein the structural resin is at least one member selected from the group consisting of homopolymers and copolymers of alpha-olefins and of 1,3-dienes, polystyrene, and polychloroprene.

18. The process of claim 17 wherein the structural resin is a homopolymer of an alpha-olefin or a copolymer of at least two alpha-olefins.

* * * * *